US010888105B2

(12) United States Patent
Bui et al.

(10) Patent No.: US 10,888,105 B2
(45) Date of Patent: Jan. 12, 2021

(54) AVOCADO EXTRACT COMPOSITION HAS BACTERICIDAL AND ANTIVIRAL PROPERTIES AND METHOD OF MANUFACTURING THE SAME

(71) Applicant: Cu Van Bui, Binh Duong (VN)

(72) Inventors: Cu Van Bui, Binh Duong (VN); Thao Phuong To Bui, Binh Duong (VN); Hai Nam Phung, Binh Duong (VN); Phuong Hoang Truong, Binh Duong (VN)

(73) Assignee: Cu Van Bui, Binh Duong (VN)

( * ) Notice: Subject to any disclaimer, the term of this patent is extended or adjusted under 35 U.S.C. 154(b) by 0 days.

(21) Appl. No.: 16/946,225

(22) Filed: Jun. 10, 2020

(65) Prior Publication Data

US 2020/0297021 A1    Sep. 24, 2020

Related U.S. Application Data

(63) Continuation-in-part of application No. 16/026,068, filed on Jul. 3, 2018, now Pat. No. 10,743,574.

(51) Int. Cl.
| | |
|---|---|
| *A61K 36/54* | (2006.01) |
| *A23L 33/185* | (2016.01) |
| *A23L 33/18* | (2016.01) |
| *A23L 33/175* | (2016.01) |
| *A23L 33/16* | (2016.01) |
| *A23L 33/125* | (2016.01) |
| *A23L 33/155* | (2016.01) |
| *A23L 33/105* | (2016.01) |
| *A23L 19/00* | (2016.01) |
| *A23L 33/00* | (2016.01) |
| *A23L 31/00* | (2016.01) |
| *A23J 3/16* | (2006.01) |

(Continued)

(52) U.S. Cl.
CPC ............... *A23L 33/185* (2016.08); *A23J 3/16* (2013.01); *A23J 3/18* (2013.01); *A23L 3/003* (2013.01); *A23L 3/3571* (2013.01); *A23L 3/40* (2013.01); *A23L 19/01* (2016.08); *A23L 31/00* (2016.08); *A23L 33/105* (2016.08); *A23L 33/125* (2016.08); *A23L 33/155* (2016.08); *A23L 33/16* (2016.08); *A23L 33/175* (2016.08); *A23L 33/18* (2016.08); *A23L 33/40* (2016.08); *A61J 15/0003* (2013.01); *A23V 2002/00* (2013.01)

(58) Field of Classification Search
CPC ..................................................... A61K 36/54
See application file for complete search history.

(56) References Cited

PUBLICATIONS

Logaraj et al., "Rheological behaviour of emulsions of avocado and watermelon oils during storage," Food Chem 106:937-943, 2008.*

* cited by examiner

*Primary Examiner* — Rosanne Kosson

(57) ABSTRACT

The present invention relates to the provision of a bactericidal, antiviral preparation obtained from the process of forming a homogeneous solution mixture by mixing an emulsion of butter extract. The method of making this composition is a systematic technical solution to create a multi-polar substance that can dissolve easily in water but still has to be soluble in oil, along with an osmotic substance that dissolves the lipid layer capsid inactivates the virus. Compositions obtained from this method have the effect of bactericidal, antiviral, environmental treatment—deodorizing—anti-pollution in order to meet the urgent needs of people, society and environment.

12 Claims, 3 Drawing Sheets

(51) Int. Cl.
*A23J 3/18* (2006.01)
*A23L 3/00* (2006.01)
*A23L 3/3571* (2006.01)
*A23L 3/40* (2006.01)
*A61J 15/00* (2006.01)

AVOCADO EXTRACT COMPOSITION HAS BACTERICIDAL AND ANTIVIRAL PROPERTIES AND METHOD OF MANUFACTURING THE SAME

FIELD OF THE INVENTION

The present invention relates generally to bactericidal and virus resistance solutions, environmental treatment (deodorizing, anti-pollution). More specifically, the present invention relates to methods and processes for creating avocado extract composition and other ingredients.

BACKGROUND ART

Currently, air pollution is at an alarming level. According to a World Health Organization's May 2018 report, about 7 million people worldwide die each year from air pollution. Accordingly, 90% of the population on earth is breathing "dirty" air, especially pollution is concentrated in Asia and Africa. Therefore, to limit bacterial respiratory diseases, the virus that produces polluted air enters the body through direct skin or respiratory contact. Penetration of bacteria and viruses by using known chemicals including Alcohol, Chlorine and Chloramine B with bactericidal effect under certain conditions, namely:

The bactericidal ability of alcohol depends on the alcohol content. Alcohol content from 90° to 99.9° low bactericidal capacity, whereas alcohol content from 50° to 70° is high bactericidal ability.
  a) For chlorine and chlorine-containing compounds, bactericidal by oxidation mechanism of atomic oxygen.
  b) The bactericidal ability of Chloramine B is similar to that of chlorine and chlorine-containing compounds; however, the bactericidal mechanism of Chloramine B is by the oxidation of chlorine.

In addition, the design of a full body disinfection chamber is one of the research topics related to the medical field that is of interest to countries around the world. The whole body sterilization chamber has a single or double chamber structure depending on the purpose of the manufacturer.
  a) For the design of one chamber operating by spraying a solution of bactericidal compounds.
  b) For the design of two interconnected chambers, including the first chamber spraying ozone gas at a dose of 0.12 ppm/30 seconds, then the second chamber spraying water droplets with a particle size of 5 μm, and spray time in 30 seconds.

All the methods mentioned above meet the ability to kill bacteria when spraying, spraying directly on the skin. However, the ability to kill viruses has not yet been met and does not guarantee safety for users. For example: ozone is harmful to human health, especially to the elderly, children and the sick; or alcohol, chlorine and chlorine compounds are harmful to the skin, clothing when sprayed on the body if the dose used is not appropriate.

According to U.S. Pat. No. 10,575,521 issued on Mar. 3, 2020, the invention refers to a compound that inhibits germination of bacteria and antibacterial extracted from avocado.

According to CN Patent No. CN105342886 (A), the invention refers to the hand washing compound extracted from avocado oil, including the raw materials of the following ingredients: 6-10 parts avocado oil, 6-10 mineral oil part, 0.5-1.5 parts trietanolamin and hexanediol stearate 4-8 parts, alcohol 6-10 parts, water 150-170 parts. The patented avocado oil hand wash can clean your hands, nourish, nourish and moisturize the skin and inhibit bacteria.

The above inventions meet the specific purposes and requirements of a technical solution. However, the disclosure of the invention does not address the adjustment of the ingredients parameters contained in an antibacterial preparation derived from. At the same time, using hexane and methanol as two main solvents to extract the antibacterial compounds from avocado requires high investment costs for high-tech equipment and labor, which is the reason for the high production cost production leads to a high inoculate price.

Therefore, it is necessary to have bactericidal, antiviral, and anti-air preparations to be environmentally friendly and safe for users.

Furthermore, what is needed to have a method to create bactericidal, antiviral and air-pollutant preparations with a composition of mainly avocado extracts and safe emulsifiers. Simultaneous treatment of unpleasant odors, bacteria derived from inorganic and organic compounds, polar and non-polar compounds, with the effect of detoxifying the air for a long time, completely replacing All preparations have a structure that works according to the odor-masking mechanism, passively absorb odors or oxidize some odorant compounds.

Finally, what is need to provide a method of creating disinfectant, antiviral, and air pollution preparations, including the number of different ingredients involved in mixing and integrating to create bactericidal, antiviral, and anti-air pollution preparations with different activities.

This invention provides solutions to achieve the above goals. Moreover, this invention is a continuation of the patent "Air deodorant from avocado" patented in Vietnam, with patent number 1-0015826.

SUMMARY OF THE INVENTION

Accordingly, an objective of the present invention is to provide a bactericidal, antiviral composition obtained from the process of forming a homogeneous solution mixture by mixing an emulsion of the avocado extract with at least four different solutions including solutions containing saturated fatty acids ("solution 1"), solutions containing unsaturated fatty acids ("solution 2"), aromatic extract solutions ("solution 3") and preservative solution ("solution 4") in a specific order with a defined percentage (%) of the total weight of a -derived preparation containing Antibacterial, antiviral effect.

Another objective of the present invention is to provide an antimicrobial, antiviral preparation consisting of four blends of solutions mixed together to obtain a homogeneous solution mixture, namely:

solution 1 includes: a polar solvent of the first percentage (%) by weight; the second component of avocado saturated fatty acid with a second percentage (%) by weight; an emulsifier with a third percentage (%) by weight; an osmotic ingredient has a fourth percentage (%) by weight; a fifth Phospholipid ingredient (%) by weight;

solution 2 includes: a surfactant ingredient with a sixth percentage (%) by weight; a component of unsaturated fatty acids extracted from avocado with the seventh percent (%) by weight; a Glycolipid ingredient with an eighth percent (%) by weight;

solution 3 includes: a ninth essential oil component (%) by weight, and a tenth percentile polar solvent component (%) by weight;

solution 4 includes: a preservative ingredient of the eleventh percentile (%) by weight and a metal reducing agent twelfth percent (%) by weight;

where, the percentage (%) by weight is determined by the sum from the first percentage (%) to the twelfth percent (%), plus the percentage (%) of the avocado extract emulsion and the percentage (%) of the solvent is 100% sufficient water.

Yet another objective of the present invention is to provide an antibacterial and antiviral compositions including: an ethanol content having 5%-20% by weight; a composition of total saturated fatty acids (Palmitic Acid, Stearic Acid, Myristic Acid) and unsaturated fatty acids (Oleic Acid, Linoleic Acid, α-Linoleic Acid) having 0.3%-1% by weight; a Twin-80 ingredient having 0.02%-0.04% weight; a component PEG-400 (Poly Ethylene Glycol-400) having 0.01%-0.02% weight; a component of phospholipid having 0.003%-0.004% weight; a Triethanolamine ingredient having 0.13%-0.45% by weight; a Monoethanolamides ingredient having 0.13%-0.3% by weight; a glycolipid composition having 0.004%-0.005% by weight; a Menthol ingredient having 0.02% of weight; one component of Sodium Benzoate having 0.06%-0.1% by weight, one component of Disodium EDTA (EthylenDiaminoTetraAcetate Disodium) having 0.06%-0.1% by weight, and an ingredient of emulsion extract solution having 4%-6% by weight.

In view of the foregoing, another objective of the present invention is to provide a process to create antibacterial and antiviral preparations includes the following steps:

(i) Prepare materials: an avocado extract emulsion and four other blending solutions including solutions containing saturated fatty acids, solutions containing unsaturated fatty acids, solutions for aromatic extracts, and preservatives;

in which, prepare solution 1 by performing a blend of Ethanol, Twin-80 and a mixture of three saturated fatty acids Palmitic Acid, Stearic Acid, Myristic Acid at a temperature of 65° C., combined stirring at an average speed of 40 rpm for 5 minutes; then continue adding PEG solution and stirring phospholipid for 15 minutes;

in which, prepare solution 2 by mixing water, Triethanolamine and Monoethanolamides at 55° C. and stirring for 5 minutes; then continue to add the mixture of three unsaturated fatty acids Oleic Acid, Linoleic Acid, α-Linoleic Acid stir for 5 minutes and finally add glycolipid stirring continue for 5 minutes;

in which, prepare solution 3 by dissolving Menthol and Ethanol at room temperature for 5 minutes;

in which, prepare solution 4 by dissolving water and Twin-80 at 55° C., combining stirring for 10 minutes; then add Sodium Benzoate and Disodium EDTA at 55° C. combined with stirring for 5 minutes;

(ii) mix the solutions prepared in step i) in two stages:

stage 1: create a homogeneous solution by mixing the prepared solutions in the order that the first solution is the solution containing saturated fatty acids, the second one is the solution containing the unsaturated fatty acids, the third solution is an aromatic extract solution and finally, the fourth solution is a solution stored; all are mixed at temperatures of 50° C.-60° C., preferably 55° C. with stirring for 15 minutes;

stage 2: Make foundation mixture by mixing a homogeneous solution in phase 1 with an emulsion of avocado extract at a temperature of 60° C.-70° C., preferably 65° C. combined with stirring for 15 minutes;

(iii) adjust the pH and ethanol content of the foundation mixture in step ii) namely: use sodium bicarbonate or nitric acid to adjust the pH in the range of 5.5-6.5, preferably pH=6. Using deionized water and ethanol to adjust the ethanol content, in which the ethanol content directly affects the activity of the obtained composition:

Ethanol content from 4.5% to 5.5%, the obtained composition has a deodorizing activity and anti-air pollution higher than the ability to kill bacteria, antiviral;

Ethanol content from 6% to 16%, the obtained composition in addition to the ability to deodorize against air pollution, the bactericidal and antiviral activity is highly effective.

Another objective of the present invention is to provide an antibacterial, antiviral preparation, which has four different formulas depending on the relative percentage (%) of each ingredient, which can be used for resistance bactericidal, antiviral, deodorant and prevent airborne hazards directly affecting the human body through respiration and exposure.

Another purpose of the invention is to provide an antibacterial, antiviral effect for more than an hour, purify the air within 5 seconds at an appropriate dose without causing discomfort before and after use, and do not cause skin irritation to the user.

Finally, the purpose of the invention is to provide a simple and cost-effective implementation method for creating the bactericidal and antiviral preparations described above including forming a solution mixture homogeneous by mixing the avocado extract with phospholipids, glycolipids and at least four types of substances including surfactants, emulsifiers, osmotic agents and polar solvents in a specific order with each component fraction determined by percentage (%) compared to the total weight of antibacterial and antiviral extract preparations.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Figure 1:
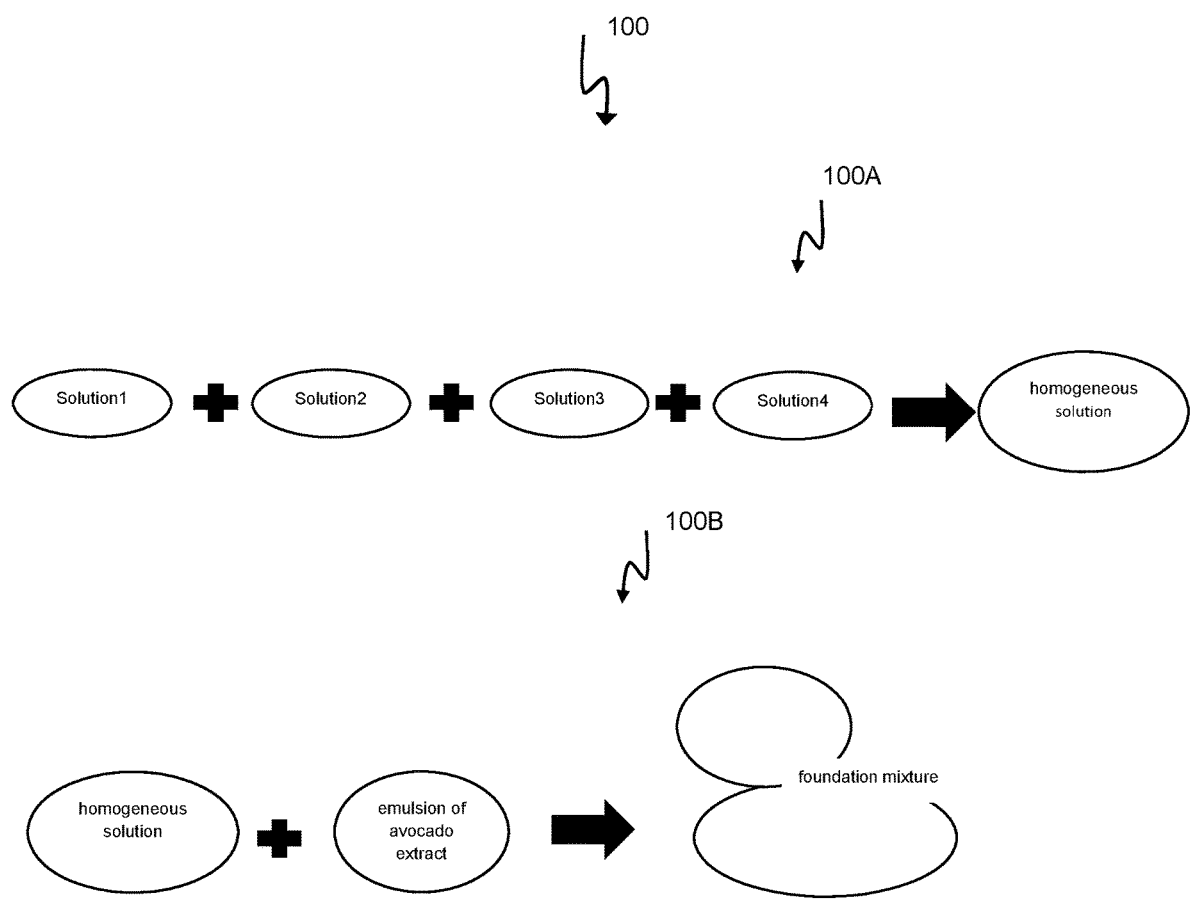
FIG. 1 is a conceptual block diagram illustrating the principle of making the antibacterial, antiviral composition in accordance with an exemplary embodiment of the present invention

One embodiment of the invention is now described with reference to FIG. 1. FIG. 1 illustrates a conceptual block diagram of a method 100 including a first stage 100A and a second stage 100B of manufacturing antibacterial and antiviral composition in accordance with an exemplary embodiment of the present invention.

In the first stage of 101, a mixture of at least four solutions from solution 1 to solution 4 is intended to dilute, prolong the time and increase deodorizing, bactericidal, and antiviral activity; to create a homogeneous solution mixture. In many aspects of the present invention, a homogeneous solution is defined as a mixture with the following functions: (1) increasing deodorizing, bactericidal, and antiviral activity; (2) acts as a lipid capsid soluble solvent, has an affinity; (3) act as a reactant to uniformly dissolve the extract components and other complementary substances (%) by weight. Consequently, a homogeneous solution mixture is created as a reactant allowing emulsifiers, osmotic agents, polar solvents, phospholipids, glycolipids, and other aromatic extracts to be mixed to form ingredients bactericidal, the antiviral composition of the invention.

Within the scope of the present invention, the term "homogeneously dissolved" includes the following meanings.

(a) A mixture of homogeneous solutions that completely dissolve the composition of emulsifiers, osmotic agents, surfactants, polar solvents, and saturated and unsaturated fatty acids having the correct percentage (%) by weight;

(b) A mixture of homogeneous solutions that completely dissolve the composition of soluble aromatic extracts and the composition of other supplements the correct percentage (%) by weight, does not retain any major fragrance of disinfectant bacteria, antiviral that the invention wants to mention;

(c) Homogeneous solution mixes act as a reactant allowing the addition of ingredients to contribute their chemical and physical properties to create a new preparation;

(d) A mixture of homogeneous solutions chemically bonds with other complementary ingredients such as ionization reactions, covalent reactions, reducing reactions, replacement reactions and rearrangement reactions to form a new chemical composition.

Still with FIG. 1, continue to the second stage of 100B, when the mixture of the homogeneous solution is mixed with the composition of the avocado emulsion solution the correct predetermined percentage (%) compared to the total weight amount of bactericidal and antiviral composition of the present invention. In particular, an emulsion of the avocado extract is added or reacted or dissolve uniformly with the homogeneous solution mixture by a magnetic stirrer.

Figure 2:
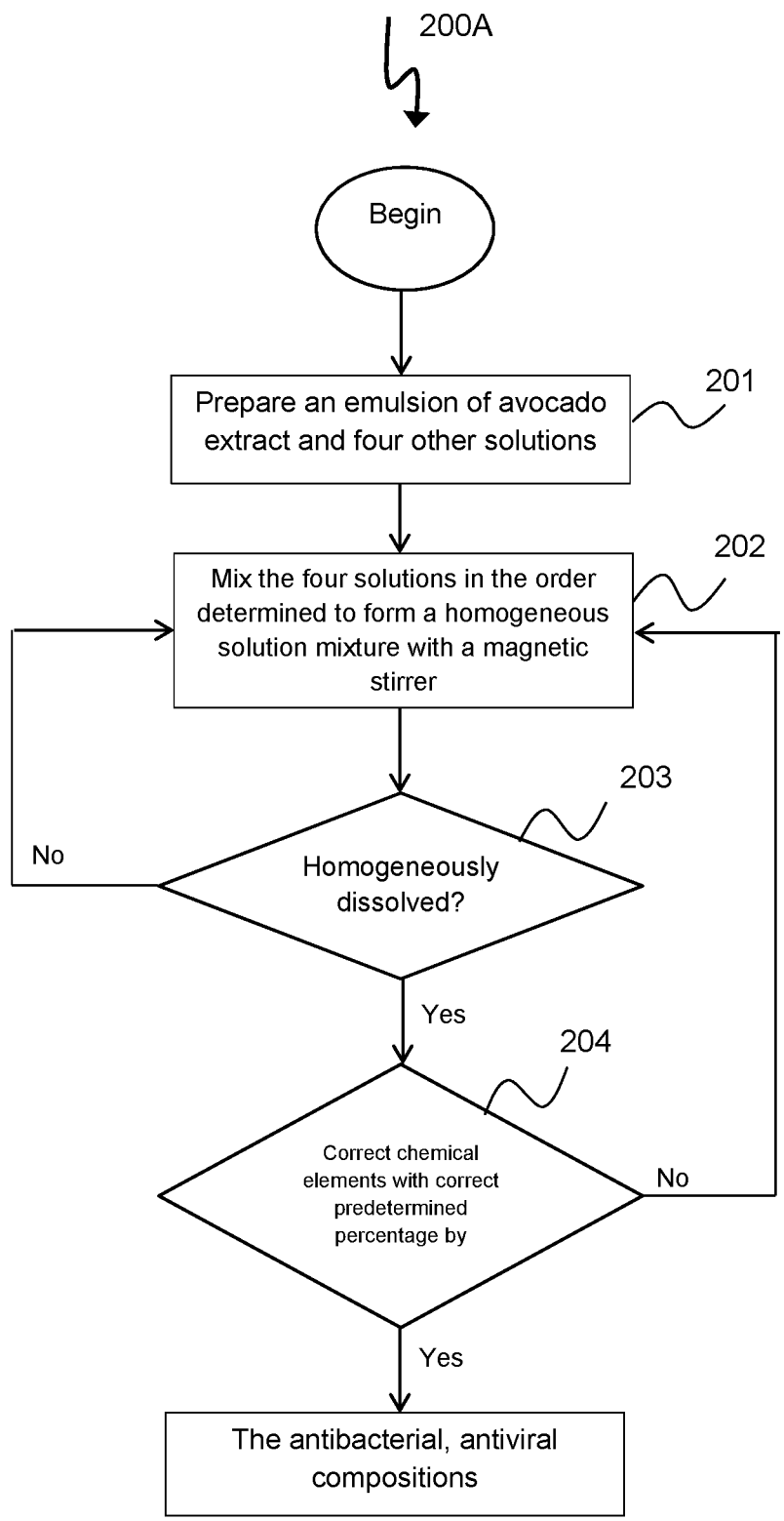
FIG. 2 is a flowchart illustrating a flowchart of a general method of manufacturing the antibacterial, antiviral composition based on the above principle in accordance with an exemplary embodiment of the present invention.

Now referring to FIG. 2, method of manufacturing the antibacterial, antiviral composition ("method 200") based on the above principle in accordance with an exemplary embodiment of the present invention. In particular, method 200 includes the following steps:

At step 201, all the solutions from 1 to 4, and the avocado extract emulsion are carefully prepared and stored in separate instruments. It should be noted that avocado extracts emulsion and solutions can be used in the present invention. Avocado-emulsifying emulsion is a plant material that can be chopped/or not shredded and soaked in a liquid such as water or solvent for a long time to extract the necessary compound components from the infused avocado into the liquid.

At step 202, the mixing of at least four solutions from solution 1 to solution 4 is intended to dilute, prolong the time and increase the deodorizing, bactericidal, and antiviral activity; to create a homogeneous solution mixture. The four different types of specific solutions are listed in Table 1 below and will be discussed later. However, in an exemplary plan of the invention, each solution is mixed in a particular order. It should be noted that when four types of solutions are not added in a particular order. It should be noted that when four solutions are not added in the specific order described, the final product will not have the chemical components listed in Table 2 below. Therefore, the final product will not have deodorizing, bactericidal, and antiviral properties. Step 203 is performed by a magnetic stirrer. Magnetic stirrer has been known in previous art so the description of the structure and its operating principle will not be described in detail in the invention.

At step 203, if the mixture mixing solutions 1 to 4 is not uniformly dissolved in the temporary mixture, step 202 is repeated with a magnetic stirrer until homogeneous conditions are reached.

At step 204, mix the avocado emulsion solution with a homogeneous solution that is checked for the correct predetermined chemical compositions as a percentage (%) by weight. Percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%. Step 204 can be done by mass spectrometers and other similar devices.

At step 205, if a predetermined composition of chemical compounds is found and/or does not have the correct percentage (%) by weight then step 204 is repeated until the correct predetermined percentage (%) by weight is achieved.

Figure 3:
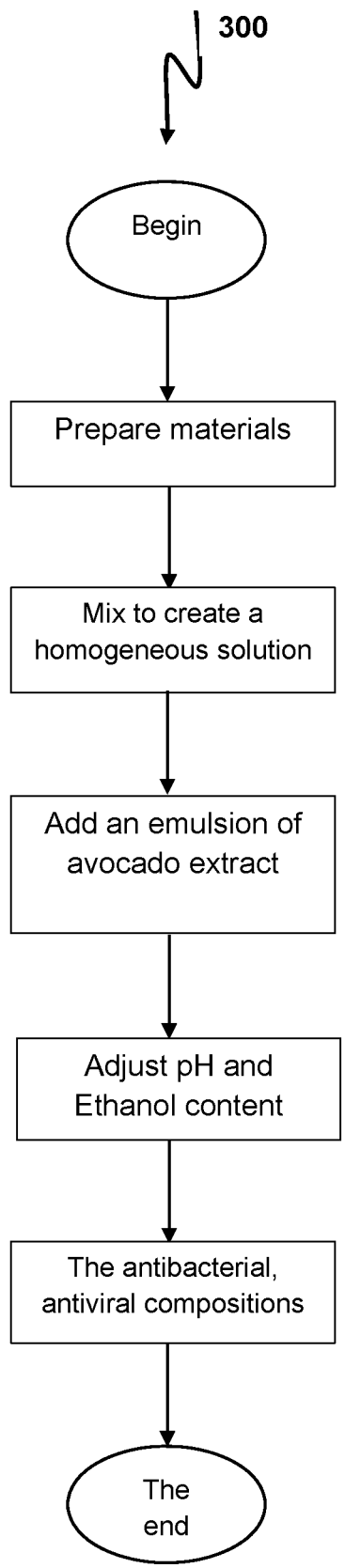
FIG. 3 is a flowchart illustrating a specific process of manufacturing the antibacterial, antiviral composition in accordance with an exemplary embodiment of the present invention.

Now referring to FIG. 3, the manufacturing process the antibacterial, antiviral composition ("process 300") in accordance with an exemplary embodiment of the present invention, including the steps:

(i) Prepare materials: an emulsion of avocado extract and four other mixing solutions, including solution 1 is a solution containing saturated fatty acids, solution 2 contains unsaturated fatty acids, solution 3 is aromatic extract solution, solution 4 is the preservative solution. In an exemplary embodiment of the present invention, all four formulations of antibacterial and antiviral composition is comprised of 4% to 6% by weight of an emulsion of extract.

solution 1 includes: a polar solvent of the first percentage (%) by weight; the second component of avocado saturated fatty acid with a second percentage (%) by weight; an emulsifier with a third percentage (%) by weight; an osmotic ingredient has a fourth percentage (%) by weight; a fifth Phospholipid ingredient by weight. In an exemplary embodiment of the present invention, all four formulations of solution 1 of antibacterial, antiviral preparations including 5%-20% by weight of the polar solvent, ethanol; 0.15%-0.5% by weight of saturated fatty acid mixture; 0.01%-0.02% by weight Twin-80; 0.01%-0.02% by weight PEG-400 and 0.003%-0.004% by weight. In an exemplary embodiment of the present invention, preparation of solution 1 by performing a blend of Ethanol, Twin-80 and a mixture of three saturated fatty acids Palmitic Acid, Stearic Acid, Myristic Acid at a temperature of 65° C., combined stirring at an average speed of 40 rpm for 5 minutes; then continue adding PEG solution and stirring phospholipid for 15 minutes; where the weight of the three saturated fatty acids is equal;

solution 2 includes: a surfactant ingredient with a sixth percentage (%) by weight; a component of unsaturated fatty acids extracted from avocado with the seventh percent (%) by weight; a Glycolipid ingredient with an eighth percent (%) by weight. In an exemplary embodiment of the present invention, all four formulas to create solution 2 of antibacterial and antiviral preparations including 0.15%-0.5% unsaturated fatty acid weight and 0.004%-0.005% by weight glycolipid; 0.13%-0.3% by weight Mono ethanol amine. According to the embodiment of the present invention, formula 3 and formula 4 of bactericidal and antiviral preparations, the composition of solution 2 includes 0% by weight of Triethanolamine. According to the embodiment of the present invention, preparation of solution 2 by mixing water, Triethanolamine and Mono ethanol amine at 55° C. and stirring for 5 minutes; then continue to add the mixture of three unsaturated fatty acids Oleic Acid, Linoleic Acid, α-Linoleic Acid stir for 5 minutes and finally add glycolipid stirring continue for 5 minutes; where the weight of the three unsaturated fatty acids is equal;

solution 3 includes: a ninth essential oil component (%) by weight, and a tenth percentile polar solvent component (%) by weight. According to the embodiment of the present invention, formula 2 and formula 4 of the bactericidal, antiviral and antiviral compositions, the composition of solution 3 consists of 0% by weight Menthol and 0% by weight of ethanol. In an exemplary embodiment of the present invention, preparation of solution 3 by dissolving Menthol and Ethanol at room temperature for 5 minutes;

solution 4 includes: a preservative ingredient of the eleventh percentile (%) by weight and a metal reducing agent twelfth percent (%) by weight. According to the embodiment of the present invention, all four formulas to prepare composition solution 4 of antibacterial and antiviral composition including 0.01%-0.02% of Twin-80 weight; 0.06%-0.1% by weight Sodium Benzoate and 0.06%-0.1% by weight Disodium EDTA. According to the embodiment of the present invention, prepare solution 4 by dissolving water and Twin-80 at 55° C., combining stirring for 10 minutes; then add Sodium Benzoate and Disodium EDTA at 55° C. combined with stirring for 5 minutes.

According to the embodiment of the present invention, all four formulas for preparation of an emulsion of avocado extracts of antibacterial and antiviral composition have a proportion of 4%-6% by weight.

According to the embodiment of the present invention, the percentage (%) by weight is determined by the sum from the first percentage (%) to the twelfth percent (%), plus the percentage (%) of the avocado extract emulsion and the percentage (%) of the solvent is 100% sufficient water.

(ii) Mix the solutions prepared in step i) in two stages:
stage 1: create a homogeneous solution by mixing the prepared solutions in the order determined respectively solution 1, solution 2, solution 3 and finally solution 4 at a temperature of 50° C.-60° C., best 55° C. with combined stirring for 15 minutes;
stage 2: Make foundation mixture by mixing a homogeneous solution in phase 1 with an emulsion of avocado extract at a temperature of 60° C.-70° C., preferably 65° C. combined with stirring for 15 minutes.

(iii) Adjust the pH and ethanol content of the foundation mixture in step ii) namely: use sodium bicarbonate or nitric acid to adjust the pH in the range of 5.5-6.5, preferably pH=6. Using deionized water and ethanol to adjust the ethanol content, in which the ethanol content directly affects the activity of the obtained composition: Ethanol content from 4.5% to 5.5%, the obtained composition has a deodorizing activity and anti-air pollution higher than the ability to kill bacteria, antiviral; Ethanol content from 6% to 16%, the obtained composition in addition to the ability to deodorize against air pollution, the bactericidal and antiviral activity is highly effective.

According to the embodiment of the present invention, antibacterial and antiviral compositions ("MMS compositions") obtained from the process 300 including: an ethanol content having 5%-20% by weight; a composition of total saturated fatty acids (Palmitic Acid, Stearic Acid, Myristic Acid) and unsaturated fatty acids (Oleic Acid, Linoleic Acid, α-Linoleic Acid) having 0.3%-1% by weight; a Twin-80 ingredient having 0.02%-0.04% weight; a component PEG-400 (Poly Ethylene Glycol-400) having 0.01%-0.02% weight; a component of phospholipid having 0.003%-0.004% weight; a Triethanolamine ingredient having 0.13%-0.45% by weight; a Mono ethanol amine ingredient having 0.13%-0.3% by weight; a glycolipid composition having 0.004%-0.005% by weight; a Menthol ingredient having 0.02% of weight; one component of Sodium Benzoate having 0.06%-0.1% by weight, one component of Disodium EDTA (EthylenDiaminoTetraAcetate Disodium) having 0.06%-0.1% by weight, and an ingredient of emulsion extract solution having 4%-6% by weight.

TABLE 1

Mixed solutions components of the MMS Composition

| | Percentage (%) Formulation | | | |
|---|---|---|---|---|
| Name of solutions | First formulation | Second formulation | Third formulation | Fourth formulation |
| Solution 1 | 13.6%-18.1% | 13.6%-18.1% | 13.6%-18.1% | 13.6%-18.1% |
| Solution 2 | 0.5%-71.9% | 0.5%-71.9% | 0.3%-71.7% | 0.3%-71.7% |

TABLE 1-continued

Mixed solutions components of the MMS Composition

| Name of solutions | Percentage (%) Formulation | | | |
|---|---|---|---|---|
| | First formulation | Second formulation | Third formulation | Fourth formulation |
| Solution 3 | 0.9%-10% | 0% | 0.9%-10% | 0% |
| Solution 4 | 0.1%-4.6% | 0.1%-4.6% | 0.1%-4.6% | 0.1%-4.6% |
| Emulsion solution extracted from avocado | 4%-6% | 4%-6% | 4%-6% | 4%-6% |

TABLE 2

Medicinal Chemical Components of the MMS Composition

| No. | Name of Medicinal Components | W/W (%) |
|---|---|---|
| 1 | Ethanol | 5%-20% |
| 2 | Saturated fatty acids | 0.15%-0.5% |
| 3 | Unsaturated fatty acids | 0.15%-0.5% |
| 4 | Twin-80 | 0.02%-0.04% |
| 5 | PEG-400 | 0.01%-0.02% |
| 6 | Phospholipid | 0.003%-0.004% |
| 7 | Glycolipid | 0.004%-0.005% |
| 8 | Triethanolamine | 0.13%-0.45% |
| 9 | Mono ethanol amine | 0.13%-0.3% |
| 10 | Menthol | 0%-0.02% |
| 11 | Sodium Benzoate | 0.06%-0.1% |
| 12 | Disodium EDTA | 0.06%-0.1% |

The following analysis results of the bactericidal and deodorizing abilities of MMS bio-products have been created through the method of the invention.

TABLE 3

Analytical results of bactericidal properties of MMS compositions

| Test criteria | Methods of analysis | Microbiological concentration tested | Microorganism alive | Result | Unit |
|---|---|---|---|---|---|
| Antibacterial activity | Vietnamese pharmacopoeia | Vietnamese pharmacopoeia | Vietnamese pharmacopoeia | | |
| *Bacillus subtilis* subsp. *Spizenii* ATCC 6633 | Vietnamese pharmacopoeia | 6,000,000 | 0 | 99.99 | % |
| *Candida albicans* ATCC 10231 | Vietnamese pharmacopoeia | 9,800,000 | 0 | 99.99 | % |
| *Staphylococcus aureus* | Vietnamese pharmacopoeia | 4,300,000 | 0 | 99.99 | % |
| *Escherichia coli* ATCC 25922 | Vietnamese pharmacopoeia | 8,000,000 | 0 | 99.99 | % |

TABLE 6

Results of deodorizing analysis of MMS compositions

| No | Test location | $NH_3$ content before and after the test (QCVN 06:2009/BTNMT) 0.2 mg/m³ | $H_2S$ content before and after the test (QCVN 06:2009/BTNMT) 0.042 mg/m³ | Processing rate |
|---|---|---|---|---|
| 1 | The breeding area in Binh Duong province | 6.35/0.14 | 1.8/0.026 | Treated 98% for $NH_3$ Treated 98.6% for $H_2S$ |
| 2 | Da-Phuoc landfill in Ho Chi Minh City | 9.128/0.248 | 0.094/0.032 | Treated 98% for $NH_3$ Low treatment for $H_2S$ |
| 3 | Trash waste in Giong Trom district, Ben Tre province | 0.54/0.15 | 0.30/0.09 | Treated 73% for $NH_3$ Treated 70% for $H_2S$ |
| 4 | Hazardous medical waste of Urenco 13 company, Hanoi in VN | — | 684.55/0.00 | Treated 100% for $NH_3$ |

TABLE 6-continued

Results of deodorizing analysis of MMS compositions

| No | Test location | NH$_3$ content before and after the test (QCVN 06:2009/BTNMT) 0.2 mg/m$^3$ | H$_2$S content before and after the test (QCVN 06:2009/BTNMT) 0.042 mg/m$^3$ | Processing rate |
|---|---|---|---|---|
| 5 | Odor treatment in bauxite mining areas in Dak Nong province | — | 0.562/0.027 | Treated 96% for NH$_3$ and H$_2$S |

The example is made according to the embodiment of the present invention.

According to the embodiment of the present invention, the production method produces 1 liter of MMS composition by the first formula including the following steps:

(i) Prepare materials: an emulsion of avocado extract and four other mixing solutions, including solution 1, solution 2, solution 3 and solution 4;

prepare solution 1 by mixing 150 g of Ethanol with 2,5 g of the saturated fatty acid mixture (Palmitic Acid, Stearic Acid, Myristic Acid), in which the weight of each saturated fatty acid is equal; all were mixed at 65° C. combined stirring at an average speed of 40 rpm for 5 minutes. After that, continue adding 0.035 g of phospholipids and adding stirring PEG solution for 15 minutes; in which PEG-400 solution by dissolving 0,2 g PEG with 50 g of water;

prepare solution 2 by mixing 800 g of water with 1,5 g of Tri-ethanol amine and 1,5 g of Mono ethanol amine at 550 C and stirring for 5 minutes. Then continue to add 2.5 g of the mixture of three unsaturated fatty acids Oleic Acid, Linoleic Acid, α-Linoleic Acid, in which the weight of each saturated fatty acid is equal; all were mixed for 5 minutes and finally added 0.045 g Glycolipid stirring continues for 5 minutes;

prepare the third solution by dissolving 0.2 g of Menthol with 10 g of ethanol solution at room temperature for 5 minutes;

prepare the fourth solution by mixing 50 g of water with 0.2 g of Twin-80 at 550 C and stirring for 10 minutes. Then continue adding 0.7 g Sodium Benzoate and 0.7 g Disodium EDTA at 550 C combined with stirring for 5 minutes;

prepare 50 g of an emulsion of the avocado extract.

(ii) mix the solutions prepared in step i) in two stages:

stage 1: create a homogeneous solution by mixing the prepared solutions in the order determined solution 1, solution 2, solution 3 and solution 4 at 55° C. with a combination of stirring in 15 minutes;

stage 2: Make a foundation mixture by mixing a homogeneous solution in phase 1 with 50 g of an emulsion of avocado extract prepared in step i) at 65° C. and stirring for 15 minutes;

(iii) Adjust the pH and ethanol content of the foundation mixture in step ii) namely: use sodium bicarbonate or nitric acid to adjust the pH in the range of 5.5-6.5, preferably pH=6. Using deionized water and ethanol to adjust the ethanol content, in which the ethanol content directly affects the activity of the obtained composition: Ethanol content from 4.5% to 5.5%, the obtained composition has a deodorizing activity and anti-air pollution higher than the ability to kill bacteria, antiviral; Ethanol content from 6% to 16%, the obtained composition in addition to the ability to deodorize against air pollution, the bactericidal and antiviral activity is highly effective.

According to the embodiment of the present invention, the production method produces 1 liter of MMS composition by the second formula including the following steps:

i) Prepare materials: an emulsion of avocado extract and four other mixing solutions, including solution 1, solution 2 and solution 4;

prepare solution 1 by mixing 150 g of Ethanol with 2.5 g of the saturated fatty acid mixture (Palmitic Acid, Stearic Acid, Myristic Acid), in which the weight of each saturated fatty acid is equal; all were mixed at 65° C. combined stirring at an average speed of 40 rpm for 5 minutes. After that, continue adding 0.035 g of phospholipids and adding stirring PEG solution for 15 minutes; in which PEG-400 solution by dissolving 0.2 g PEG with 50 g of water;

prepare solution 2 by mixing 800 g of water with 1.5 g of Tri-ethanol amine and 1.5 g of Mono ethanol amine at 550 C and stirring for 5 minutes. Then continue to add 2.5 g of the mixture of three unsaturated fatty acids Oleic Acid, Linoleic Acid, α-Linoleic Acid, in which the weight of each saturated fatty acid is equal; all were mixed for 5 minutes and finally added 0.045 g Glycolipid stirring continues for 5 minutes;

prepare the fourth solution by mixing 50 g of water with 0.2 g of Twin-80 at 550 C and stirring for 10 minutes. Then continue adding 0.7 g Sodium Benzoate and 0.7 g Disodium EDTA at 550 C combined with stirring for 5 minutes;

prepare 50 g of an emulsion of the avocado extract;

(ii) mix the solutions prepared in step i) in two stages:

stage 1: create a homogeneous solution by mixing the prepared solutions in the order determined solution 1, solution 2 and solution 4 at 55° C. with a combination of stirring in 15 minutes;

stage 2: Make a foundation mixture by mixing a homogeneous solution in phase 1 with 50 g of an emulsion of avocado extract prepared in step i) at 65° C. and stirring for 15 minutes;

(iii) Adjust the pH and ethanol content of the foundation mixture in step ii) namely: use sodium bicarbonate or nitric acid to adjust the pH in the range of 5.5-6.5, preferably pH=6. Using deionized water and ethanol to adjust the ethanol content, in which the ethanol content directly affects the activity of the obtained composition: Ethanol content from 4.5% to 5.5%, the obtained composition has a deodorizing activity and anti-air pollution higher than the ability to kill bacteria, antiviral; Ethanol content from 6% to 16%, the obtained composition in addition to the ability to deodorize against air pollution, the bactericidal and antiviral activity is highly effective.

According to the embodiment of the present invention, the production method produces 1 liter of MMS composition by the third formula including the following steps:

(i) Prepare materials: an emulsion of avocado extract and four other mixing solutions, including solution 1, solution 2, solution 3 and solution 4;

prepare solution 1 by mixing 150 g of Ethanol with 2,5 g of the saturated fatty acid mixture (Palmitic Acid, Stearic Acid, Myristic Acid), in which the weight of each saturated fatty acid is equal; all were mixed at 65° C. combined stirring at an average speed of 40 rpm for 5 minutes. After that, continue adding 0.035 g of phospholipids and adding stirring PEG solution for 15 minutes; in which PEG-400 solution by dissolving 0,2 g PEG with 50 g of water;

prepare solution 2 by mixing 800 g of water with 1,5 g of Mono ethanol amine at 55° C. and stirring for 5 minutes. Then continue to add 2.5 g of the mixture of three unsaturated fatty acids Oleic Acid, Linoleic Acid, α-Linoleic Acid, in which the weight of each saturated fatty acid is equal; all were mixed for 5 minutes and finally added 0.045 g Glycolipid stirring continues for 5 minutes;

prepare the third solution by dissolving 0.2 g of Menthol with 10 g of ethanol solution at room temperature for 5 minutes;

prepare the fourth solution by mixing 50 g of water with 0.2 g of Twin-80 at 55° C. and stirring for 10 minutes. Then continue adding 0.7 g Sodium Benzoate and 0.7 g Disodium EDTA at 550 C combined with stirring for 5 minutes;

prepare 50 g of an emulsion of the avocado extract.

(ii) mix the solutions prepared in step i) in two stages:

stage 1: create a homogeneous solution by mixing the prepared solutions in the order determined solution 1, solution 2, solution 3 and solution 4 at 55° C. with a combination of stirring in 15 minutes;

stage 2: Make a foundation mixture by mixing a homogeneous solution in phase 1 with 50 g of an emulsion of avocado extract prepared in step i) at 65° C. and stirring for 15 minutes;

(iii) Adjust the pH and ethanol content of the foundation mixture in step ii) namely: use sodium bicarbonate or nitric acid to adjust the pH in the range of 5.5-6.5, preferably pH=6. Using deionized water and ethanol to adjust the ethanol content, in which the ethanol content directly affects the activity of the obtained composition: Ethanol content from 4.5% to 5.5%, the obtained composition has a deodorizing activity and anti-air pollution higher than the ability to kill bacteria, antiviral; Ethanol content from 6% to 16%, the obtained composition in addition to the ability to deodorize against air pollution, the bactericidal and antiviral activity is highly effective.

According to the embodiment of the present invention, the production method produces 1 liter of MMS composition by the fourth formula including the following steps:

i) Prepare materials: an emulsion of avocado extract and four other mixing solutions, including solution 1, solution 2 and solution 4;

prepare solution 1 by mixing 150 g of Ethanol with 2,5 g of the saturated fatty acid mixture (Palmitic Acid, Stearic Acid, Myristic Acid), in which the weight of each saturated fatty acid is equal; all were mixed at 65° C. combined stirring at an average speed of 40 rpm for 5 minutes. After that, continue adding 0.035 g of phospholipids and adding stirring PEG solution for 15 minutes; in which PEG-400 solution by dissolving 0,2 g PEG with 50 g of water;

prepare solution 2 by mixing 800 g of water with 1,5 g of Mono ethanol amine at 55° C. and stirring for 5 minutes. Then continue to add 2.5 g of the mixture of three unsaturated fatty acids Oleic Acid, Linoleic Acid, α-Linoleic Acid, in which the weight of each saturated fatty acid is equal; all were mixed for 5 minutes and finally added 0.045 g Glycolipid stirring continues for 5 minutes;

prepare the fourth solution by mixing 50 g of water with 0.2 g of Twin-80 at 55° C. and stirring for 10 minutes. Then continue adding 0.7 g Sodium Benzoate and 0.7 g Disodium EDTA at 550 C combined with stirring for 5 minutes;

prepare 50 g of an emulsion of the avocado extract;

(ii) mix the solutions prepared in step i) in two stages:

stage 1: create a homogeneous solution by mixing the prepared solutions in the order determined solution 1, solution 2 and solution 4 at 55° C. with a combination of stirring in 15 minutes;

stage 2: make a foundation mixture by mixing a homogeneous solution in phase 1 with 50 g of an emulsion of avocado extract prepared in step i) at 65° C. and stirring for 15 minutes;

(iii) Adjust the pH and ethanol content of the foundation mixture in step ii) namely: use sodium bicarbonate or nitric acid to adjust the pH in the range of 5.5-6.5, preferably pH=6. Using deionized water and ethanol to adjust the ethanol content, in which the ethanol content directly affects the activity of the obtained composition: Ethanol content from 4.5% to 5.5%, the obtained composition has a deodorizing activity and anti-air pollution higher than the ability to kill bacteria, antiviral; Ethanol content from 6% to 16%, the obtained composition in addition to the ability to deodorize against air pollution, the bactericidal and antiviral activity is highly effective.

The efficiency of the invention:

Antimicrobial, antiviral composition can solve major social problems that are happening on a global scale. It is able to cope with the disease Coronavirus which is extremely dangerous to human health, pets, . . . and limits the odor from the environment that is increasingly polluted. As follows:

a) Relieves pain, heals wounds, and stops bleeding very quickly (regenerates, nourishes damaged cells with healing time from 10 h to 24 h maximum). Time to relieve pain and stop bleeding in about 10 to 15 seconds. Time wound up young skin a maximum of 20 hours.

b) The bactericidal ability has been certified through testing of 310,000,000 bacteria samples with absolute kill results.

c) Eliminate bacteria completely, prevent the penetration and spread of bacteria and viruses. Eliminate all stinking, toxic pollutants from organic substances, inorganic substances, chemical emissions such as gasoline, pesticides . . . Return the inherent purity of the air, protect Good for the respiratory system.

Moreover, antibacterial and antiviral compositions can survive in the air for 1 to 24 hours; and at the same time capable of performing the following functions:

a) It is possible to replace disinfectant and disinfectant in the operating room to make the operating room aseptic, clean air, doctors, and patients breathe in clean space, without any side effects.

b) It is possible to replace disinfectants and disinfect wounds for patients so that the patients do not get much pain, the wounds heal quickly and the space of things, people are always clean and breathing is healthy.

c) Used to combat the dangers from the air. When using an antibacterial preparation, antiviral sprays into any space will help prevent cross-respiratory transmission and be purified within 5 seconds, returning air to cleanness.

In addition, in a space in public places such as schools, hospitals, supermarkets, accommodations, offices, offices, factories, factories, etc., or where there are parking lots for cars and planes, etc., then when using bactericidal or antiviral compositions, there will be no cross-infection from bacterial, viral respiratory diseases.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A bactericidal, antiseptic, deodorizing and antiviral composition obtained from the process of forming a homogeneous solution mixture by mixing an emulsion of an avocado extract with at least four different solutions including (a) a solution containing saturated fatty acids, (b) a solution containing unsaturated fatty adds, (c) an aromatic extract solution and (d) a preservative solution in the aforementioned order;

(i) wherein said solution containing saturated fatty acids comprises a polar solvent having a first percentage (%) by weight; a saturated fatty acid from avocado having a second percentage (%) by weight; an emulsifier having a third percentage (%) by weight; an osmotic ingredient having a fourth percentage (%) by weight; and a Phospholipid ingredient having a fifth percentage (%) by weight;

(ii) wherein said solution containing unsaturated fatty acids comprises a surfactant ingredient having a sixth percentage (%) by weight; unsaturated fatty acids extracted from avocado having the seventh percentage (%) by weight; a Glycolipid ingredient having an eighth percentage (%) by weight;

(iii) wherein said aromatic extract solution comprises an essential oil component having a ninth percentage (%) by weight, and a polar solvent having a tenth percentage (%) by weight;

(iv) wherein said preservative solution comprises a preservative ingredient having an eleventh percentage (%) by weight and a metal reducing agent having a twelfth percentage (%) by weight;

(v) wherein each percentage (%) by weight is determined by the sum from the first percentage (%) to the twelfth percentage (%), plus the percentage (%) of the avocado extract emulsion and the percentage (%) of sufficient water to total 100%.

2. The bactericidal and antiviral composition of claim 1, wherein the deodorizing, bactericidal, antiseptic, and antiviral activities depend on the percentage (%) of the weight of each ingredient and each of solutions (a)-(d), wherein each solution is used to make a formula, wherein the third formula is stronger than the first formula, the fourth formula is stronger than the second formula and the first formula is stronger than the second formula; and wherein the comparative factor is deodorizing, bactericidal, antiseptic, and antiviral activity.

3. The bactericidal and antiviral composition of claim 2, wherein the first formula comprises
    (a) an ethanol content having 5%-20% by weight;
    (b) total saturated fatty acids (comprising Palmitic Acid, Stearic Acid, and Myristic Acid) and unsaturated fatty acids (comprising Oleic Acid, Linoleic Acid, and α-Linoleic Acid) having 0.3%-1% by weight;
    (C) Tween-8O having 0.02%-0.04% weight;
    (d) PEG-400 (Poly Ethylene Glycol-400) having 0.01%-0.02% weight;
    (e) phospholipid having 0.003%-0.004% weight;
    (f) Triethanolamine having 0.13%-0.45% by weight;
    (g) Monoethanolamine having 0.13%-0,3% by weight;
    (h) a glycolipid having 0.004%-0.005% by weight;
    (i) Menthol having 0.02% by weight;

(j) Sodium Benzoate having 0.06%-0.1% by weight;
(k) Disodium EDTA (ethylenediaminetetraacetate Disodium) having 0.06%-0.1% by weight; and
(l) an avocado extract emulsion having 4%-6% by weight.

4. The bactericidal and antiviral composition of claim 2, wherein said second formula comprises
   (a) an ethanol content having 5%-20% by weight;
   (b) total saturated fatty acids (comprising Palmitic Acid, Stearic Acid, and Myristic Acid) and unsaturated fatty acids (comprising Oleic Acid, Linoleic Acid, and α-Linoleic Acid) having 0.3%-1% by weight;
   (c) Tween-80 having 0.02%-0.04% weight;
   (d) PEG-400 (Poly Ethylene Glycol-400) having 0.01%-0.02% weight;
   (e) phospholipid having 0.003%-0.004% weight;
   (f) Triethanolamine having 0.13%-0.45% by weight;
   (g) Monoethanolamine having 0.13%-0.3% by weight;
   (h) a glycolipid having 0.004%-0.005% by weight;
   (i) Menthol having 0% by weight;
   (j) Sodium Benzoate having 0.06%-0.1% by weight;
   (k) Disodium EDTA (ethylenediaminetetraacetate Disodium) having 0.06%-0.1% by weight; and
   (l) avocado extract emulsion having 4% 6% by weight.

5. The bactericidal and antiviral composition of claim 2, wherein said third formula comprises
   (a) an ethanol content having 5%-20% by weight;
   (b) total saturated fatty acids (comprising Palmitic Acid, Stearic Acid, and Myristic Acid) and unsaturated fatty acids (comprising Oleic Acid, Linoleic Acid, and α-Linoleic Acid) having 0.3%-1% by weight;
   (c) Tween-80 having 0.02%-0.04% weight;
   (d) PEG-400 (Poly Ethylene Glycol-400) having 0.01%-0.02% weight;
   (e) phospholipid having 0.003%-0.004% weight;
   (f) Triethanolamine having 0% by weight;
   (g) Monoethanolamine having 0.13%-0.3% by weight;
   (h) a glycolipid having 0.004%-0.005% by weight;
   (i) Menthol having 0.02% by weight;
   (j) Sodium Benzoate having 0.06%0.1% by weight;
   (k) Disodium EDTA (ethylenediaminetetraacetate Disodium) having 0.06%-1% by weight; and
   (l) an avocado extract emulsion having 4%-6% by weight.

6. The bactericidal and antiviral composition of claim 2, wherein said fourth formula comprises
   (a) an ethanol content having 5%-20% by weight;
   (b) total saturated fatty acids (comprising Palmitic Acid; Stearic Acid, and Myristic Acid) and unsaturated fatty acids (comprising Oleic Acid, Linoleic Acid, and α-Linoleic Acid) having 0.3%-1% by weight;
   (c) Tween-80 having 0.02%-0.04% weight;
   (d) PEG-400 (Poly Ethylene Glycol-400) having 0.01%-0.02% weight;
   (e) phospholipid having 0.003%-0.004% weight;
   (f) Triethanolamine having 0% by weight;
   (g) Monoethanolamine having 0.13%-0.3% by weight;
   (h) a glycolipid having 0.004%-0.005% by weight;
   (i) Menthol having 0% by weight;
   (j) Sodium Benzoate having 0.06%-0.1% by weight;
   (i) Disodium EDTA (ethylenediaminetetraacetate Disodium) having 0.06%-0.1% by weight; and
   (k) an avocado extract emulsion having 4%-6% by weight.

7. A process of manufacturing the bactericidal, antiseptic, deodorizing and antiviral composition of claim 1, the process comprising steps performed in the following specific order:
   (i) Preparing materials by mixing an avocado extract emulsion and four other blending solutions including
     (a) a solution containing saturated fatty acids, (b) a solution containing unsaturated fatty acids, (c) an aromatic extract solution and (d) a preservative solution in the aforementioned order;
   (A) wherein said solution containing saturated fatty acids is made by mixing Ethanol, Tween-80 and a mixture of three saturated fatty acids—Palmitic Acid, Stearic Acid, and Myristic Acid at a temperature of 65° C., stirring at an average speed of 40 rpm for 5 minutes; then adding the phospholipid in a PEG solution and stirring 15 minutes;
   (B) wherein said solution containing unsaturated fatty acids is made by mixing water, Triethanolamine and Monoethanolamine at 55° C. and stirring for 5 minutes; then by adding, the mixture of three unsaturated fatty acids—Oleic Acid, Linoleic Acid, and α-Linoleic Acid, stirring for 5 minutes, adding the glycolipid and stirring for an additional 5 minutes;
   (C) wherein said aromatic extract solution is made by mixing Menthol and Ethanol at room temperature for 5 minutes;
   (D) wherein said preservative solution is made by mixing water and Tween-80 at 55° C. and stirring for 10 minutes; then by adding Sodium Benzoate and Disodium EDTA at 55° C. and stirring for 5 minutes;
   (ii) mixing the materials in step i) in two stages:
   stage 1: creating a homogeneous solution by mixing the prepared materials in the order that the first solution is the solution containing saturated fatty acids, the second solution is the solution containing unsaturated fatty acids, the third solution is an aromatic extract solution and finally, the fourth solution is a solution preservative solution; all are mixed at temperatures of 50° C. 60° C. with stirring for 15 minutes;
   stage 2: Making a foundation mixture by mixing a homogeneous solution in stage 1 with the avocado extract emulsion at a temperature of 60° C.-70° C., combined with stirring for 15 minutes;
   (iii) adjusting the pH and ethanol content of the foundation mixture in step ii):
   wherein said adjusting the pH to 5.5-6.5 comprises adding sodium bicarbonate or nitric acid;
   wherein the ethanol content is adjusted to 4.5-16% by adding deionized water or methanol;
   wherein, when the ethanol content is 4.5-5.5%, the composition has deodorizing activity and and anti-air pollution activity;
   wherein, when the ethanol content is 6-16%, the composition has bactericidal activity and anti-viral activity.

8. The process of claim 7, wherein said deodorizing, bactericidal, antiseptic, and antiviral activities depend on the percentage (%) of the weight of each ingredient.

9. The process of claim 7 wherein the process makes a composition of a first formula, wherein the composition of the first formula comprises:
   (a) an ethanol content having 5%-20% by weight;
   (b) total saturated fatty acids (comprising Palmitic Acid, Stearic Acid, and Myristic Acid) and unsaturated fatty acids (comprising Oleic Acid, Linoleic Acid, and a α-Linoleic Acid) having 0.3%-1% by weight;
(c) Tween-80 having 0.02%-0.04% weight;
(d) PEG-400 (Poly Ethylene Glycol-400) having 0.01%-0.02% weight;
(e) phospholipid having 0.003%-004% weight;
(f) Triethanolamine having 0.13%-0.45% by weight;
(g) Monoethanolamine having 0.13%-0.3% by weight;
(h) a glycolipid having 0.004%-0.005% by weight;
(i) Menthol having 0.02% by weight;
(j) Sodium Benzoate having 0.06%-0.1% by weight;
(k) Disodium EDTA (ethylenediaminetetraacetate) having 0.06%-0.1% by weight; and
(l) an avocado extract emulsion having 4%-6% by weight.

10. The process of claim 7 wherein the process makes a composition of a second formula, wherein the composition of the second formula comprises:
(a) an ethanol content having 5%-20% by weight;
(b) total saturated fatty acids (comprising Palmitic Acid, Stearic Acid, and Myristic Acid) and unsaturated fatty acids (comprising Oleic Acid, Linoleic Acid, and α-Linoleic Acid) having 0.3%-1% by weight;
(c) Tween-80 having 0.02%-0.04% weight;
(d) PEG-400 (Poly Ethylene Glycol-400) having 0.01%-0.02% weight;
(e) phospholipid having 0.003%-0.004% weight;
(f) Triethanolamine having 0.13%-0.45% by weight;
(g) Monoethanolamine having 0.13%-0.3%, by weight;
(h) a glycolipid having 0.004%-0.005% by weight;
(i) Menthol having 0% by weight;
(j) Sodium Benzoate having 0.06%-0.1% by weight;
(k) Disodium EDTA (ethylenediaminetetraacetate) having 0.06%-0.1% by weight; and
(l) an avocado extract emulsion having 4%-6% by weight.

11. The process of claim 7 wherein the process makes a composition of a third formula, wherein the composition of the third formula comprises:
(a) an ethanol content having 5%-20% by weight;
(b) total saturated fatty acids (comprising Palmitic Acid, Stearic Acid, and Myristic Acid) and unsaturated fatty acids (comprising Oleic Acid, Linoleic Acid, and α-Linoleic Acid) having 0.3%-1% by weight;
(c) Tween-80 having 0.02%-0.04% weight;
(d) PEG-400 (Poly Ethylene Glycol-400) having 0.01%-0.02% weight;
(e) phospholipid having 0.003%-0.004% weight;
(f) Triethanolamine having 0% by weight;
(g) Monoethanolamine having 0.13%-0.3% by weight;
(h) a glycolipid having 0.004%-0.005% by weight;
(i) Menthol having 0.02% by weight;
(j) Sodium Benzoate having 0.06%-0.1% by weight;
(k) Disodium EDTA (ethylenediaminetetraacetate) having 0.06%-0.1% by weight; and
(l) an avocado extract emulsion having 4%-6% by weight.

12. The process of claim 7 wherein the process makes a composition of a fourth formula, wherein the composition of the fourth formula comprises:
(a) an ethanol content having 5%-20% by weight;
(b) total saturated fatty acids (comprising Palmitic Acid, Stearic Acid, and Myristic Acid) and unsaturated fatty acids (comprising Oleic Acid, Linoleic Acid, and α-Linoleic Acid) having 0.3%-1% by weight;
(c) Tween-80 having 0.02%-0.04% weight;
(d) PEG-400 (Poly Ethylene Glycol-400) having 0.01%-0.02% weight;
(e) phospholipid having 0.003%-0.004% weight;
(f) Triethanolamine having 0% by weight;
(g) Monoethanolamine having 0.13%-0.3% by weight;
(h) a glycolipid having 0.004%-0.005% by weight;
(i) Menthol having 0% by weight;
(j) Sodium Benzoate having 0.06%-0.1% by weight;
(k) Disodium EDTA (ethylenediaminetetraacetate) having 0.06%-0.1% by weight; and
(l) an avocado extract emulsion having 4%-6% by weight.

* * * * *